United States Patent

Korb et al.

Patent Number: 6,143,896
Date of Patent: Nov. 7, 2000

[54] PROCESS FOR THE ALKYLATION OF ALKYL-OR BENZYLCYANOGEN DERIVATIVES IN THE PRESENCE OF TRIALKYLAMINES OR TRIALKYLPHOSPHINES

[75] Inventors: Gerhard Korb, Hainburg; Hans-Wolfram Flemming, Usingen; Rudolf Lehnert, Mainz, all of Germany

[73] Assignee: Aventis Pharma Deutschland GmbH, Frankfurt am Main, Germany

[21] Appl. No.: 09/212,585

[22] Filed: Dec. 16, 1998

[30] Foreign Application Priority Data

Dec. 17, 1997 [DE] Germany .............. 197 56 091
Jan. 29, 1998 [DE] Germany .............. 198 03 408

[51] Int. Cl.⁷ .................. C07D 211/34; C07C 255/03
[52] U.S. Cl. ............. 546/230; 546/246; 558/328
[58] Field of Search ................... 558/327, 357, 558/328; 546/246, 230

[56] References Cited

U.S. PATENT DOCUMENTS

| | | | |
|---|---|---|---|
| 3,668,255 | 6/1972 | Meuly et al. | 260/586 |
| 4,254,129 | 3/1981 | Carr et al. | |
| 5,739,375 | 4/1998 | Fischer . | |

FOREIGN PATENT DOCUMENTS 0 671 379  9/1995  European Pat. Off. .
22 06 778  8/1973  Germany .

OTHER PUBLICATIONS

Smith et al., "Relative Nucleophilicites of Carbanions Derived From α–Substituted Phenylacetonitriles", J. Org. Chem., 36(15):2132–2137 (1971).

Trivedi et al., "Inhibitors of Acyl–CoA:Cholesterol Acyltransferase. 4. A Novel Series of Urea ACAT Inhibitiors as Potential Hypocholesterolemic Agents", J. Med. Chem., 36:3300–3307 (1993).

English Derwent Abstract of DE 22 06 778. Aug. 16, 1973.

*Primary Examiner*—Joseph K. McKane
*Assistant Examiner*—Ebenezer Sackey
*Attorney, Agent, or Firm*—Finnegan, Henderson, Farabow, Garrett, and Dunner, L.L.P.

[57] ABSTRACT

A process for the alkylation of compounds of the formula II

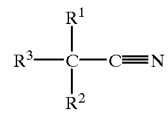

(II)

where the reaction with the alkylating agent is carried out in the presence of a base and a trialkylamine and/or trialkylphosphine.

31 Claims, No Drawings

PROCESS FOR THE ALKYLATION OF ALKYL-OR BENZYLCYANOGEN DERIVATIVES IN THE PRESENCE OF TRIALKYLAMINES OR TRIALKYLPHOSPHINES

This application claims the benefit of priority to German patent application serial no. 19756091.1, filed Dec. 17, 1997, and no. 19803408.3, filed Jan. 29, 1998. Both applications are specifically incorporated herein by reference.

European Patent Application no. EP 0 671 379, which is specifically incorporated herein by reference, describes a process for the methylation of organic compounds in the presence of trialkylamines and dimethyl carbonate. The yield of α,α-dimethylbenzyl cyanide is 29%. In addition, the alkylation of benzyl cyanide using alkylating agents such as methyl iodide or methyl chloride in the presence of strong bases such as sodium hydride, sodium amide or sodium alkoxide is described. Smith et al., J. ORG. CHEM. 36 (1971), 15, pages 2132–2137; Trivedi et al., J. MED. CHEM., EN, 36, 22, (1993), pages 3300–3307. These two publications are specifically incorporated herein by reference. Disadvantages of this reaction are the increased formation of ether products, and the formation and emission of hydrogen and ammonia together with the alkylating agent. Moreover, the strong bases have to be prepared in a manner which is ecologically and economically complex.

The object of the present invention is to find a process for alkylating the compounds of the formula II in high yields and purity.

The invention thus relates to a process for obtaining the compound of the formula I

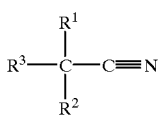

(I)

where $R^1$ is
1. $(C_1-C_{20})$-alkyl,
2. $(C_1-C_{20})$-alkyl, which is mono-, di- or trisubstituted by
    2.1. $(C_3-C_6)$-cycloalkyl,
    2.2. —OH,
    2.3. $(C_1-C_6)$-alkyl-C(O)—O—,
    2.4. $(C_1-C_6)$-alkyl-O—,
    2.5. $(C_1-C_6)$-alkyl-O—$(C_1-C_4)$-alkyl-O—,
    2.6. halogen,
    2.7. —CF$_3$,
    2.8. —CN,
    2.9. —NO$_2$,
    2.10. HO—C(O)—,
    2.11. $(C_1-C_6)$-alkyl-O—C(O)—,
    2.12. methylenedioxo,
    2.13. $R^5$—$(R^6)$N—C(O)—, in which $R^5$ and $R^6$ are identical or different and are a hydrogen atom or $(C_1-C_6)$-alkyl,
    2.14. $R^5$—$(R^6)$N—, in which $R^5$ and $R^6$ are identical or different and are a hydrogen atom or $(C_1-C_6)$-alkyl, or
    2.15. phenyl, which is unsubstituted or mono-, di- or trisubstituted independently of one another by $(C_1-C_6)$-alkyl or is substituted as described under 2.1 to 2.14,
3. $(C_2-C_{20})$-alkenyl, or
4. $(C_2-C_{20})$-alkenyl which is mono-, di- or trisubstituted independently of one another as described under 2.1 to 2.15;

$R^2$ is as defined for $R^1$ or is
1. phenyl, or
2. phenyl, which is mono-, di- or trisubstituted by
    2.1. $(C_1-C_6)$-alkyl, in which the alkyl chain is straight or branched,
    2.2. $(C_3-C_6)$-cycloalkyl,
    2.3. —OH,
    2.4. $(C_1-C_6)$-alkyl-C(O)—O—,
    2.5. $(C_1-C_6)$-alkyl-O—,
    2.6. $(C_1-C_6)$-alkyl-O—$(C_1-C_4)$-alkyl-O—,
    2.7. halogen,
    2.8. —CF$_3$,
    2.9. —CN,
    2.10. —NO$_2$,
    2.11. HO—C(O)—,
    2.12. $(C_1-C_6)$-alkyl-O—C(O)—,
    2.13. methylenedioxo,
    2.14. $R^5$—$(R^6)$N—C(O)—, in which $R^5$ and $R^6$ are identical or different and are a hydrogen atom or $(C_1-C_6)$-alkyl, or
    2.15. $R^5$—$(R^6)$N—, in which $R^5$ and $R^6$ are identical or different and are a hydrogen atom or $(C_1-C_6)$-alkyl, or $R^1$ and $R^2$ together with the carbon atom to which they are bonded and the radicals $R^3$ and —CN form a compound of the formula IV,

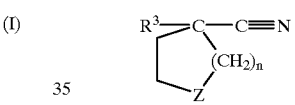

(IV)

where Z is N, O, or S, and n is 1 or 2, or when Z is N or S, Z is unsubstituted or substituted by R, in which R is $(C_1-C_6)$-alkyl, benzyl, or phenyl;

$R^3$ is
1. phenyl, or
2. phenyl, which is mono-, di- or trisubstituted by
    2.1. $(C_1-C_6)$-alkyl, in which the alkyl chain is straight or branched,
    2.2. $(C_3-C_6)$-cycloalkyl,
    2.3. —OH,
    2.4. $(C_1-C_6)$-alkyl-C(O)—O—,
    2.5. $(C_1-C_6)$-alkyl-O—,
    2.6. $(C_1-C_6)$-alkyl-O—$(C_1-C_4)$-alkyl-O—,
    2.7. halogen,
    2.8. —CF$_3$,
    2.9. —CN,
    2.10. —NO$_2$,
    2.11. HO—C(O)—,
    2.12. $(C_1-C_6)$-alkyl-O—C(O)—,
    2.13. methylenedioxo,
    2.14. $R^5$—$(R^6)$N—C(O)—, in which $R^5$ and $R^6$ are identical or different and are a hydrogen atom or $(C_1-C_6)$-alkyl, or
    2.15. $R^5$—$(R^6)$N—, in which $R^5$ and $R^6$ are identical or different and are a hydrogen atom or $(C_1-C_6)$-alkyl.

These compounds are made by a process of reacting a compound of the formula II,

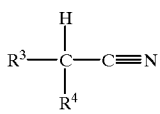

where
R³ is as defined in formula I, and
R⁴ is a hydrogen atom or is as defined for R² in formula I, and optionally, the compound of the formula II is dissolved in an organic solvent or is not dissolved in a solvent,
with an alkylating agent of the formula III, where R¹ is as defined in formula I, and X is halogen, or where 2 radicals of R¹ are bonded to the radical SO₄, or
with an alkylating agent of the formula IIIa,

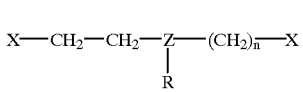

in which Z, X, R, and n are as defined above, in the presence of a base and at least one compound of the formula V or formula VI

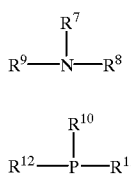

where R⁷, R⁸, R⁹, R¹⁰, R¹¹ and R¹² are identical or different and are (C₁–C₃₀)-alkyl or phenyl.

Preference is given to preparing compounds of the formula I in which
R¹ is
1. (C₁–C₆)-alkyl,
2. (C₁–C₆)-alkyl, which is disubstituted by —O—CH₃, or
3. (C₁–C₆)-alkyl, which is monosubstituted by R⁵—(R⁶)—N—, where R⁵ and R⁶ are identical or different and are hydrogen or (C₁–C₃)-alkyl;
R² is as defined for R¹ or is phenyl; or
R¹ and R² together with the carbon atom to which they are bonded and the radicals R³ and —CN form a compound of the formula IVa,

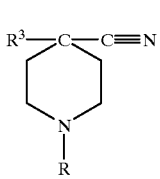

where R is (C₁–C₆)-alkyl, benzyl or phenyl; and
R³ is phenyl, which is unsubstituted or monosubstituted by (C₁–C₃)-alkyl-O—.

Advantageously, the compounds of the formula I are prepared in which
R¹ is (C₁–C₃)-alkyl, or is (C₁–C₃)-alkyl disubstituted by —O—CH₃ or —CH(CH₃)—CH₂—N—(CH₃)—CH₃;
R² is as defined for R¹ or is phenyl, or
R¹ and R² together with the carbon atom to which they are bonded form a radical of the formula IVa, in which R is —CH₃; and
R³ is phenyl, which is unsubstituted or monosubstituted by —O—CH₃.

Preference is given to using the process according to the invention for preparing compounds of the formula I where R¹ and R² are (C₁–C₆)-alkyl, and R³ is phenyl.

Particular preference is given to preparing dimethylbenzyl cyanide or 1-methyl-4-phenylpiperidine-4-carbonitrile.

The compound of the formula I is prepared by first introducing the base and the compound of the formulae V and/or VI with stirring and then adding the compound of the formula II, which has, if necessary, been dissolved beforehand in an organic solvent, and the alkylating agent, the reaction of which gives a compound of the formula I.

Per mole of the compound of the formula II, preference is given to using from about 2.1 mol to about 2.4 mol, in particular from about 2.15 mol to about 2.25 mol, of the alkylating agent of the formula II, and, per mol of the compound of the formula II, preference is given to using from about 2.5 mol to about 4 mol, in particular from about 2.8 mol to about 3.2 mol, of the base.

Per 100 percent by weight (% by wt.) of the compound of the formula II, preference is given to using from about 0.5% by wt. to about 5% by wt., in particular from about 1% by wt. to about 2% by wt. of the compound of the formulae V and/or VI.

The reaction temperature is from about 20° C. to about 100° C., preferably from about 30° C. to about 40° C. The reaction time is generally from 2 to 10 hours.

If the alkylating agent is in gaseous form, as is the case with methyl chloride (chloromethane), it is also possible to carry out the reaction at a pressure of up to 5 bar above atmospheric pressure. In the alkylating reaction with dialkyl sulfate, the methylsulfuric acid which forms during the reaction is bonded by the further addition of alkali metal hydroxide if necessary. When the reaction is complete, the compound of the formula I is isolated. For this, water is added to the mixture, and the phases which form as a result are then separated. The compound of the formula I is then obtained from the organic phase. If it appears necessary, the organic phase can be subjected to a purification procedure, such as, for example, distillation under reduced pressure, or crystallization from a solvent.

Preferred bases are alkali metal hydroxides, e.g. sodium hydroxide, potassium hydroxide and lithium hydroxide, particularly preferably sodium hydroxide. Preferred solvents are, for example: (C₅–C₇)-aliphatic and (C₆–C₈)-cycloaliphatic hydrocarbons, such as pentane, 2-methylbutane, hexane, 2,2-dimethylbutane, 2-methylpentane, 3-methylpentane, heptane, cyclohexane, methylcyclohexane, 1,2-dimethylcyclohexane and 1,3-dimethylcyclohexane; aromatic hydrocarbons, such as toluene, xylenes, ethylbenzene and isoproylbenzene; aromatic and aliphatic halogenated hydrocarbons, such as chlorobenzene, dichloromethane, dichloropropane and 1,2-dichloroethane; polyethers, such as ethylene glycol dibutyl ether, diethylene glycol ethyl tert-butyl ether, polyethylene glycol dibutyl ether, polypropylene glycol dibutyl ether, polyethylene glycol dimethyl ether, polyethylene glycol diethyl ether, polypropylene glycol diethyl ether and polypropylene glycol methyl ether; heterocyclic hydrocarbons, such as N-methylpyrrolidone and pyridine; ethers, such as tetrahydrofuran, dibutyl ether, or methyl tert-butyl ether; and also dimethyl carbonate and dimethyl sulfoxide. Suitable compounds of the formula V and/or VI are the following: trimethylamine, dimethylethylamine, triethylamine, tri-n-propylamine, triisopropylamine, tributylamine, trioctylamine, tricyclohexylamine, trihexadecylamine, diphenylmethylamine, dimethylbenzylamine, dibenzylmethylamine, tribenzylamine, or triphenylamine, or trimethylphosphine, triethylphosphine, tri-n-propylphosphine, tributylphosphine, triisopropylphosphine, trioctylphosphine, or triphenylphosphine.

It is also possible to use mixtures of the compounds of the formula V and/or VI. Preferred compounds of the formula V and/or VI are $(C_3-C_{24})$-trioctylamine or $(C_3-C_{24})$-trioctylphosphine. Particularly preferred compounds of the formula V and/or formula VI are trioctylamine, trioctylphosphine, and triethylamine.

Preferred alkylating agents are $(C_1-C_6)$-alkyl halides, such as alkyl chloride, alkyl bromide, alkyl fluoride, or alkyl iodide, in particular methyl chloride, ethyl chloride or propyl chloride; $(C_1-C_6)$-dialkyl sulfates, such as dimethyl-, diethyl-, dipropyl-, dibutyl-, dipentyl-, or dihexyl sulfate, or di-(2-chloroethyl)methylamine.

The term "halogen" is taken to mean fluorine, chlorine, bromine, or iodine. The term "alkyl" or "alkenyl" is taken to mean hydrocarbon radicals whose carbon chain is straight or branched. Cyclic alkyl radicals are, for example, 3- to 6-membered monocycles, such as cyclopropyl, cyclobutyl, cyclopentyl or cyclohexyl. In addition, the alkenyl radical can contain more than one double bond, i.e., 2, 3, or 4 double bonds.

In addition, it has sometimes proven advantageous to additionally add to the reaction mixture at least one quaternary ammonium compound and/or phosphonium compound of the formulae VII and/or VIII (VII)

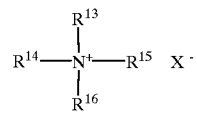

(VIII)

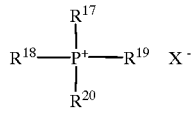

where $R^{13}$ to $R^{20}$ are identical or different and independently of one another are a) $(C_1-C_{20})$-alkyl, straight-chain or branched, b) benzyl, or c) phenyl, and $X^-$ is an anion.

It is also possible to additionally use mixtures of the compounds of the formulae VII and VIII. Preferred quaternary ammonium or phosphonium compounds of the formulae VII and VIII are methyltrioctylammonium chloride, methyltrioctylammonium hydroxide, methyltrioctylammonium chloride, methyl-tricaprylammonium hydroxide, ethyltrioctylammonium chloride, ethyl-trioctylphosphonium chloride, and hexadecyltributylphosphonium bromide: in particular methyltrioctylammonium chloride is preferred.

Per 100 mol of the compound of the formula II, preference is given to using from 10 mol to 300 mol, in particular from 100 mol to 300 mol, of the compound of the formulae VII and/or VIII.

The compounds of the formulae VII and VIII are, for example, added prior to the compound of the formula II.

The starting substances for the alkylating reaction according to the invention can be prepared by processes known from the literature, for example, by cyanolysis of the corresponding halogen compounds.

The products of the process are desired compounds for the preparation of many subsequent products, e.g., for the preparation of antiallergically effective medicaments such as 4-[4-[4-(hydroxydiphenyl)-1-piperidinyl]-1-hydroxybutyl]-α,α-dimethylphenylacetic acid. See U.S. Pat. No. 4,254,129, which is specifically incorporated herein by reference.

Advantageous features of the present invention are the high yields and the high purity of the prepared products.

EXAMPLE 1

Preparation of dimethylbenzyl cyanide

A reactor was charged with 1416 g of sodium hydroxide solution, 33% strength, and 425 g of caustic soda. 6 g of trioctylamine was then added to this solution, and then 400 g of benzyl cyanide and 380 g of chloromethane were reacted in this mixture at from 20° C. to 40° C. with stirring at superatmospheric pressure. After the internal pressure had dropped to below 0.5 bar, the residual pressure was released. 2000 ml of water were then added, and the mixture was briefly stirred and allowed to settle, and then the phases were separated. The organic phase was distilled under reduced pressure to give 485.5 g of pure dimethylbenzyl cyanide having a content of more than 99%, as determined by gas chromatography "GC". This is 98% of theory based on benzyl cyanide used. The content of monomethylbenzyl cyanide and unreacted benzyl cyanide was in each case below 0.1%. The content of hydrolysis products such as phenylacetic acid was below the detection limit.

GC Parameters

| | |
|---|---|
| Separation column: | HP1, 25 m long |
| Temperature of injection block: | 250° C. |
| Start temperature: | 50° C. |
| Heating rate: | 10° C./min |
| Final temperature: | 250° C. |
| Carrier gas: | Helium or nitrogen |
| Split ratio: | 1:100 |
| Detector: | FID |
| Amount injected: | 3 μl (5% strength solution in toluene) |
| Retention times: | |
| Benzyl cyanide | about 6.9 min |
| Monomethylbenzyl cyanide | about 7.5 min |
| Dimethylbenzyl cyanide | about 8.0 min |

EXAMPLE 2

Preparation of 1-methyl-4-phenylpiperidine-4-carbonitrile (Dolantin nitrile)

A reactor was charged with 1160 g of sodium hydroxide solution, 33% strength, and 184 g of caustic soda. 5 g of trioctylamine and 15 g of methyltrioctylammonium chloride were added to this solution. 117 g of benzyl cyanide and a solution of 163.8 g of di-(2-chloroethyl)methylamine in 820 g of toluene were then simultaneously metered in at from 60° C. to 80° C. with thorough stirring. The mixture was then stirred for a further 2 to 4 hours. 2000 ml of water were then added, and the mixture was briefly stirred, and the phases which formed were separated from one another. An initially acidic, and subsequently alkaline extraction separated the product from the catalyst (trioctylamine, methyl-trioctylammonium chloride) and organic impurities. The toluene was then distilled off from the organic phase under reduced pressure. The distillation residue was then further purified by distillation under a high vacuum at a pressure of less than 1 mbar. The distillate obtained was 180 g of 1-methyl-4-phenylpiperidine-4-carbonitrile having a content of more than 99% (determined by gas chromatography (GC)). This corresponds to a yield of 90% of theory based on the benzyl cyanide used.

GC Parameters

| | |
|---|---|
| Separation column: | DB17, 30 m long |
| Temperature of injection block: | 250° C. |
| Start temperature: | 100° C. |
| Heating rate: | 10° C./min |
| Final temperature: | 250° C. |
| Carrier gas: | Helium |
| Split ratio: | 1:100 |
| Detector: | FID |
| Amount injected: | 3 μl (5% strength solution in toluene) |
| Retention times: | |
| Benzyl cyanide | about 9 min |
| Dolantin nitrile | about 18 min |

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoin description. All changes that come within the meaning and range of equivalency of the claims are to be embraced within their scope.

What is claimed is:

1. A process for preparing a compound of formula I

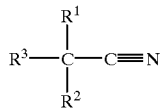

(I)

where $R^1$ is
1. $(C_1-C_{20})$-alkyl,
2. $(C_1-C_{20})$-alkyl, which is mono-, di- or trisubstituted by
   2.1. $(C_3-C_6)$-cycloalkyl,
   2.2. —OH,
   2.3. $(C_1-C_6)$-alkyl-C(O)—O—,
   2.4. $(C_1-C_6)$-alkyl-O—,
   2.5. $(C_1-C_6)$-alkyl-O—$(C_1-C_4)$-alkyl-O—,
   2.6. halogen,
   2.7. —$CF_3$,
   2.8. —CN,
   2.9. —$NO_2$,
   2.10. HO—C(O)—,
   2.11. $(C_1-C_6)$-alkyl-O—C(O)—,
   2.12. methylenedioxo,
   2.13. $R^5$—$(R^6)$N—C(O)—, in which $R^5$ and $R^6$ are identical or different and are a hydrogen atom or $(C_1-C_6)$-alkyl,
   2.14. $R^5$—$(R^6)$N—, in which $R^5$ and $R^6$ are identical or different and are a hydrogen atom or $(C_1-C_6)$-alkyl, or
   2.15. Phenyl, which is unsubstituted or mono-, di- or trisubstituted independently of one another by $(C_1-C_6)$-alkyl or is substituted as described under 2.1 to 2.14,
3. $(C_2-C_{20})$-alkenyl, or
4. $(C_2-C_{20})$-alkenyl, which is mono-, di- or trisubstituted independently of one another as described under 2.1 to 2.15;

$R^2$ is as defined for $R^1$ or is
1. phenyl, or
2. phenyl, which is mono-, di- or trisubstituted by
   2.1. $(C_1-C_6)$-alkyl, in which the alkyl chain is straight or branched,
   2.2. $(C_3-C_6)$-cycloalkyl,
   2.3. —OH,
   2.4. $(C_1-C_6)$-alkyl-C(O)—O—,
   2.5. $(C_1-C_6)$-alkyl-O—,
   2.6. $(C_1-C_6)$-alkyl-O—$(C_1-C_4)$-alkyl-O—,
   2.7. halogen,
   2.8. —$CF_3$,
   2.9. —CN,
   2.10. —$NO_2$,
   2.11. HO—C(O)—,
   2.12. $(C_1-C_6)$-alkyl-O—C(O)—,
   2.13. methylenedioxo,
   2.14. $R^5$—$(R^6)$N—C(O)—, in which $R^5$ and $R^6$ are identical or different and are a hydrogen atom or $(C_1-C_6)$-alkyl, or
   2.15. $R^5$—$(R^6)$N—, in which $R^5$ and $R^6$ are identical or different and are a hydrogen atom or $(C_1-C_6)$-alkyl;

or $R^1$ and $R^2$ together with the carbon atom to which they are bonded and the radicals $R^3$ and —CN form a compound of the formula IV,

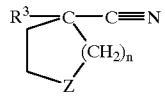

(IV)

where Z is N, O, or S, and n is 1 or 2, or when Z is N or S, Z is unsubstituted or substituted by R, in which R is $(C_1-C_6)$-alkyl, benzyl, or phenyl;

$R^3$ is
1. phenyl, or
2. phenyl, which is mono-, di- or trisubstituted by
   2.1. $(C_1-C_6)$-alkyl, in which the alkyl chain is straight or branched,
   2.2. $(C_3-C_6)$-cycloalkyl,
   2.3. —OH,
   2.4. $(C_1-C_6)$-alkyl-C(O)—O—,
   2.5. $(C_1-C_6)$-alkyl-O—,
   2.6. $(C_1-C_6)$-alkyl-O—$(C_1-C_4)$-alkyl-O—,
   2.7. halogen,
   2.8. —$CF_3$,
   2.9. —CN,
   2.10. —$NO_2$,
   2.11. HO—C(O)—,
   2.12. $(C_1-C_6)$-alkyl-O—C(O)—,
   2.13. methylenedioxo,
   2.14. $R^5$—$(R^6)$N—C(O)—, in which $R^5$ and $R^6$ are identical or different and are a hydrogen atom or $(C_1-C_6)$-alkyl, or
   2.15. $R^5$—$(R^6)$N—, in which $R^5$ and $R^6$ are identical or different and are a hydrogen atom or $(C_1-C_6)$-alkyl;

which comprises reacting a compound of the formula II,

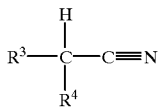
(II)

where $R^3$ is as defined in formula I, and $R^4$ is a hydrogen atom or is as defined for $R^2$ in formula I, and optionally, the compound of the formula II is dissolved in an organic solvent or is not dissolved in a solvent, with an alkylating agent of the formula III, $R^1$—X  (III)

where $R^1$ is as defined in formula I, and X is halogen or where 2 radicals of $R^1$ are bonded to the radical $SO_4$, or with an alkylating agent of the formula IIIa,

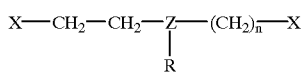
(IIIa)

where Z, X, R and n are as defined above, in the presence of an alkali metal hydroxide and at least one compound of the formula V or formula VI

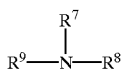
(V)

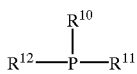
(VI)

where $R^7$, $R^8$, $R^9$, $R^{10}$, $R^{11}$ and $R^{12}$ independently of one another are identical or different and are $(C_1-C_{30})$-alkyl or phenyl.

2. A process as claimed in claim 1, wherein $R^1$ is

1. $(C_1-C_6)$-alkyl,

2. $(C_1-C_6)$-alkyl, which is disubstituted by —O—CH$_3$, or

3. $(C_1-C_6)$-alkyl, which is monosubstituted by $R^5$—$(R^6)$—N—, where $R^5$ and $R^6$ are identical or different and are hydrogen or $(C_1-C_3)$-alkyl;

$R^2$ is as defined for $R^1$ or is phenyl; or $R^1$ and $R^2$ together with the carbon atom to which they are bonded and the radicals $R^3$ and —CN form a compound of the formula IVa,

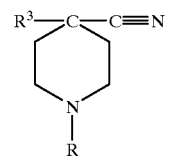
(IVa)

where R is $(C_1-C_6)$-alkyl, benzyl or phenyl; and $R^3$ is phenyl, unsubstituted or monosubstituted by $(C_1-C_3)$-alkyl-O—.

3. A process as claimed in claim 1, wherein $R^1$ is $(C_1-C_3)$-alkyl, $(C_1-C_3)$-alkyl disubstituted by —O—CH$_3$, or —CH(CH$_3$)—CH$_2$—N—(CH$_3$)—CH$_3$;

$R^2$ is as defined for $R^1$ or is phenyl; or $R^1$ and $R^2$ together with the carbon atom to which they are bonded and the radicals $R^3$ and —CN form a compound of the formula Iva, in which R is —CN$_3$; and $R^3$ is phenyl, unsubstituted or monosubstituted by —O—CH$_3$.

4. A process as claimed in claim 1, wherein the compound of the formula I is dimethylbenzyl cyanide or 1-methyl-4-phenylpiperidine-4-carbonitrile.

5. A process as claimed in claim 1, wherein the at least one compound of the formula V or VI is trimethylamine, dimethylethylamine, triethylamine, tri-n-propylamine, triisopropylamine, tributylamine, trioctylamine, tricyclohexylamine, trihexadecylamine, diphenylmethylamine, dimethylbenzylamine, dibenzylmethylamine, tribenzylamine, triphenylamine, trimethylphosphine, triethylphosphine, tri-n-propylphosphine, tributylphosphine, trioctylphosphine, triisopropylphosphine, or triphenylphosphine.

6. A process as claimed in claim 1, wherein the at least one compound of the formula V or VI is trioctylamine, trioctylphosphine, or triethylamine.

7. A process as claimed in claim 1, wherein the alkali metal hydroxide comprises sodium hydroxide, potassium hydroxide, or lithium hydroxide.

8. A process as claimed in claim 1, wherein the alkali metal hydroxide is sodium hydroxide.

9. A process as claimed in claim 1, wherein the alkylating agent comprises a $(C_1-C_6)$-alkyl halide, a $(C_1-C_6)$-dialkyl sulfate, or di-(2-chloroethyl)methylamine.

10. A process as claimed in claim 9, wherein the $(C_1-C_6)$-alkyl halide is an alkyl chloride, an alkyl bromide, or an alkyl iodide.

11. A process as claimed in claim 9, wherein the $(C_1-C_6)$-alkyl halide is methyl chloride, ethyl chloride, or propyl chloride.

12. A process as claimed in claim 9, wherein the $(C_1-C_6)$-dialkyl sulfate is dimethyl sulfate, diethyl sulfate, dipropyl sulfate, dibutyl sulfate, dipentyl sulfate, or dihexyl sulfate.

13. A process as claimed in claim 1, wherein, per mole of the compound of the formula II, from about 2.1 mol to about 2.4 mol of the alkylating agent of the formula III is used.

14. A process as claimed in claim 1, wherein, per mole of the compound of the formula II, from about 2.5 mol to about 4 mol of the alkali metal hydroxide is used.

15. A process as claimed in claim 1, wherein, per mole of the compound of the formula II, from about 2.15 mol to about 2.25 mol of the alkylating agent of the formula III is used, and, wherein per mole of the compound of the formula II, from about 2.8 mol to about 3.2 mol of the alkali metal hydroxide is used.

16. A process as claimed in claim 1, wherein, per 100 percent by weight (% by wt.) of the compound of the formula II, from about 0.5% by wt. to about 5% by wt. of the compound of the formula V or formula VI is used.

17. A process as claimed in claim 1, wherein, per 100 percent by weight (% by wt.) of the compound of the formula II, from about 1% by wt. to about 2% by wt. of the compound of the formula V or formula VI is used.

18. A process as claimed in claim 1, wherein the alkylation process is carried out at a temperature ranging from about 20° C. to about 100° C.

19. A process as claimed in claim 1, wherein the alkylation process is carried out at a temperature ranging from about 30° C. to about 40° C.

20. A process as claimed in claim 1, wherein the compound of the formula II is reacted in the presence of a compound of the formulae VII or VIII

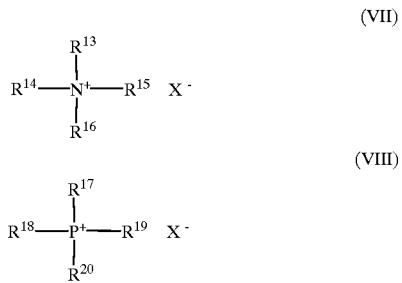

where $R^{13}$ to $R^{20}$ are identical or different and independently of one another are
  a) $(C_1-C_{20})$-alkyl, which is straight-chain or branched,
  b) benzyl, or
  c) phenyl, and
  $X^-$ is an anion.

21. A process as claimed in claim 20, wherein the compound of the formulae VII or VIII is methyltrioctylammonium chloride, methyl-trioctylammonium hydroxide, methyltricaprylammonium chloride, methyl-tricaprylammonium hydroxide, ethyltrioctylammonium chloride, ethyltrioctylphosphonium chloride, or hexadecyltributylphosphonium bromide.

22. A process as claimed in claim 20, wherein the compound of the formula VII is methyltrioctylammonium chloride.

23. A process as claimed in claim 20, wherein, per 100 mol of the compound of the formula II, from about 10 mol to about 300 mol of the compound of the formulae VII or VIII are used.

24. A process as claimed in claim 20, wherein, per 100 mol. of the compound of the formula II, from about 100 mol to about 300 mol of the compound of the formulae VII or VIII are used.

25. A process as claimed in claim 1, wherein the compound of the formula II is dissolved in a solvent comprising a $(C_5-C_7)$-aliphatic or $(C_6-C_8)$-cycloaliphatic hydrocarbon, an aromatic hydrocarbon, an aromatic or aliphatic halogenated hydrocarbon, a polyether, a heterocyclic hydrocarbon, an ether, dimethyl carbonate, or dimethyl sulfoxide.

26. A process as claimed in claim 25, wherein the $(C_5-C_7)$-aliphatic or $(C_6-C_8)$-cycloaliphatic hydrocarbon is pentane, 2-methylbutane, hexane, 2,2-dimethylbutane, 2-methylpentane, 3-methylpentane, heptane, cyclohexane, methylcyclohexane, 1,2-dimethylcyclohexane, or 1,3-dimethylcyclohexane.

27. A process as claimed in claim 25, wherein the aromatic hydrocarbon is toluene, a xylene, ethylbenzene, or isopropylbenzene.

28. A process as claimed in claim 25, wherein the aromatic or aliphatic halogenated hydrocarbon is chlorobenzene, dichloromethane, dichloropropane, or 1,2-dichloroethane.

29. A process as claimed in claim 25, wherein the polyether is ethylene glycol dibutyl ether, diethylene glycol ethyl tert-butyl ether, polyethylene glycol dibutyl ether, polypropylene glycol dibutyl ether, polyethylene glycol dimethyl ether, polyethylene glycol diethyl ether, polypropylene glycol diethyl ether, or polypropylene glycol methyl ether.

30. A process as claimed in claim 25, wherein the heterocyclic hydrocarbon is N-methylpyrrolidone or pyridine.

31. A process as claimed in claim 25, wherein the ether is tetrahydrofuran, dibutyl ether, or methyl tert-butyl ether.

* * * * *

UNITED STATES PATENT AND TRADEMARK OFFICE
CERTIFICATE OF CORRECTION

PATENT NO. : 6,143,896
DATED : November 7, 2000
INVENTOR(S) : Gerhard Korb et al.

It is certified that error appears in the above-identified patent and that said Letters Patent is hereby corrected as shown below:

Title page,
Item [54], Title, "ALKYL-OR" should read -- ALKYL- OR --.
Item [57], ABSTRACT, line 1, "II" should read -- I --; and
Line 2, delete "(II)".

Column 10,
Line 20, "formula Iva" should read -- formula IVa --.

Signed and Sealed this

Fourteenth Day of May, 2002

Attest:

JAMES E. ROGAN
*Attesting Officer*     *Director of the United States Patent and Trademark Office*